(12) United States Patent
Kahook

(10) Patent No.: US 9,980,853 B2
(45) Date of Patent: May 29, 2018

(54) NON-INVASIVE DEVICE FOR LOWERING INTRAOCULAR PRESSURE

(71) Applicant: The Regents of the University of Colorado, a body corporate, Denver, CO (US)

(72) Inventor: Malik Y. Kahook, Denver, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 0 days. days.

(21) Appl. No.: 14/829,256

(22) Filed: Aug. 18, 2015

(65) Prior Publication Data

US 2015/0351963 A1 Dec. 10, 2015

Related U.S. Application Data

(63) Continuation of application No. 12/995,175, filed as application No. PCT/US2009/045687 on May 29, 2009.

(Continued)

(51) Int. Cl.
*A61H 23/00* (2006.01)
*A61F 9/007* (2006.01)
*A61H 23/02* (2006.01)

(52) U.S. Cl.
CPC ....... *A61F 9/00781* (2013.01); *A61H 23/006* (2013.01); *A61H 23/02* (2013.01)

(58) Field of Classification Search
CPC .......... A61H 5/00; A61H 9/00; A61H 9/0007; A61H 9/005; A61H 2023/002;
(Continued)

(56) References Cited

U.S. PATENT DOCUMENTS 3,308,653 A * 3/1967 Roth ........................ A61B 3/16
600/402
4,766,904 A * 8/1988 Kozin ...................... A61B 3/16
600/405
(Continued)

FOREIGN PATENT DOCUMENTS

WO WO2006129305 * 12/2006

*Primary Examiner* — Michael Tsai
(74) *Attorney, Agent, or Firm* — Michael M. McGaw; Smith & Hopen, P.A.

(57) ABSTRACT

The present invention provides devices and methods for non-invasively lowering intraocular pressure. In particular, some non-invasive intraocular pressure lowering devices of the invention comprise an oscillating element having a proximal end and a terminal probe. Typically, the terminal probe of said oscillating element comprises a substantially non-abrasive material that is adapted to be in contact with an ocular surface without causing any significant damage to the tissue and is shaped to conform to ocular surface at the limbal region. Devices also include an oscillating mechanism that is operatively connected to the proximal end of said oscillating tip such that when oscillating mechanism is in operation said oscillating tip moves axially without damaging ocular cells. Intraocular pressure lowering devices of the present invention are capable of non-invasively transmitting mechanical force to the tissue proximate to the limbal tissue.

20 Claims, 3 Drawing Sheets

Related U.S. Application Data

(60) Provisional application No. 61/057,468, filed on May 30, 2008.

(58) Field of Classification Search
CPC .. A61H 23/006; A61H 23/02; A61H 23/0254; A61H 35/02; A61H 2205/027; A61F 2007/0004; A61F 9/00; A61F 9/007; A61F 9/00736; A61F 9/00745; A61F 9/00781; A61B 3/00; A61B 3/0083; A61B 3/10
See application file for complete search history.

(56) References Cited

U.S. PATENT DOCUMENTS

| | | | | |
|---|---|---|---|---|
| 5,372,595 A | * | 12/1994 | Gaasterland | ............ A61F 9/008 606/13 |
| 2003/0195438 A1 | * | 10/2003 | Petillo | ...................... A61H 5/00 601/15 |
| 2008/0051681 A1 | * | 2/2008 | Schwartz | ............ A61F 9/00781 601/2 |
| 2010/0076419 A1 | * | 3/2010 | Chew | ...................... A61F 9/008 606/6 |

* cited by examiner

NON-INVASIVE DEVICE FOR LOWERING INTRAOCULAR PRESSURE

CROSS-REFERENCE TO RELATED APPLICATIONS

This application is a continuation of U.S. application Ser. No. 12/995,175, filed Nov. 29, 2010, which was the National Stage of International Application No. PCT/US2009/045687, filed May 29, 2009, which claims the benefit of U.S. Provisional Application No. 61/057,468, filed May 30, 2008.

FIELD OF INVENTION

The present invention relates to devices and methods for non-invasively lowering intraocular pressure.

BACKGROUND OF THE INVENTION

Glaucoma is a leading cause of world-wide blindness. Increased intraocular pressure (IOP) has been identified in multiple studies as a leading cause of glaucomatous optic neuropathy (GON). While many glaucoma risk factors, such as family history of glaucoma, advanced age, and race have been identified, increased IOP is the only risk factor modifiable by medical or surgical intervention. Decreasing IOP has been linked to slower progression of visual field loss in ocular hypertensive patients as well as in various forms of glaucoma. While often effective at lowering IOP, the use of medical and surgical modalities to treat glaucoma is associated with unwanted side-effects, poor compliance with topical drop therapy and potential for infection, pain and loss of vision from invasive procedures.

Accordingly, there is a need for a non-invasive method for lowering intraocular pressure.

SUMMARY OF THE INVENTION

Some aspects of the invention provide noninvasive devices and methods for lowering IOP. These aspects of the invention can be applied repeatedly and result in fewer side-effects relative to many conventional treatments currently used to lower IOP. Other advantages of devices and methods of the invention include, but are not limited to, the ease of use and adaptability to other applications. Moreover, the skill level needed to perform methods of the invention or to use devices of the invention is much lower than other conventional treatment procedures, such as microsurgery.

Some aspects of the invention provide a non-invasive IOP lowering device comprising an oscillating element and an oscillating mechanism that is operatively connected to the oscillating element. The oscillating element comprises a proximal end and a terminal probe. The proximal end of the oscillating element is operatively connected to the oscillating mechanism such that when the oscillating mechanism is in operation the oscillating element moves axially. Such movement of the oscillating element exerts non-invasive mechanical forces on the ocular tissue. The terminal probe can comprise a substantially non-abrasive material that is adapted to be in contact with an ocular surface and can be shaped to conform to the ocular surface often at the anatomic limbus of the eye. In operation, the IOP lowering device transmits a non-invasive mechanical force to the tissue proximate to the limbus. Often, mechanical force is transmitted to cells comprising trabecular meshwork, Schlemm's canal, surrounding tissues and/or a combination thereof.

The non-invasive IOP lowering device repeatedly applies force to tissue at set frequency and amplitude. In some embodiments, the frequency of the oscillating mechanism is from about 1 Hz to about 40 kHz. Typically from 100 Hz to about 1 kHz, often from about 100 Hz to about 900 Hz.

In other embodiments, the frequency of oscillation can be adjusted from at least about 1 Hz to about 1 kHz. Typically from 100 Hz to about 900 Hz, often from about 100 Hz to about 900 Hz.

Yet in other embodiments, the amplitude of oscillation can range from about 0.1 mm to about 1 mm. Typically, movement of the oscillating element is limited substantially to its axial direction so as to limit motion of the eye and focus the mechanical force on the targeted tissue typically without leading to any significant ocular vibration. In other embodiments, the oscillating element can move transversally. Often the amplitude of oscillation ranges from about 0.2 mm to about 0.8 mm, more often from about 0.3 mm to about 0.7 mm, and in many cases about 0.5 mm.

Still in other embodiments, the amplitude of oscillation is adjustable from about 0.1 mm to about 1 mm axially. Typically the amplitude of oscillation can be adjusted from about 0.2 mm to about 0.8 mm, and more often from about 0.3 mm to about 0.7 mm.

Generally, the material for the oscillating probe tip (i.e., terminal probe tip) is chosen such that it does not cause damage to the tissue that it comes in contact with. In some embodiments, the material for the oscillating probe tip comprises plastic, metallic, silicone, polypropylene, or other non-abrasive materials, or a combination thereof.

The oscillating probe tip is designed to allow focused transmission of mechanical force to a designated ocular surface. The shape of the oscillating probe tip can be a circle, ellipse, oval, or any other shape as long as it can transmit mechanical force to a desired ocular surface in a non-invasive manner. In many instances, the oscillating probe tip is in the shape of a circle, ellipse or oval. In general, the area of the terminal probe that contacts the ocular surface has a mean diameter of from about 0.1 mm to about 6 mm, typically from about 0.2 mm to about 3 mm, often from about 0.2 mm to about 1 mm, and more often from about 0.3 mm to about 0.7 mm. In some particular embodiments, the oscillating probe tip has a mean diameter of about 0.5 mm.

Other aspects of the invention provide methods for reducing the IOP of a subject. The methods generally comprise applying non-invasive mechanical force to a tissue proximate to the limbal tissue under conditions sufficient to cause decrease in IOP of the subject. Such force is applied by contacting the ocular surface and exerting a sufficient amount of force to cause the force to be transmitted to the tissue proximate to the limbal tissue. In some instances, the non-invasive mechanical force is applied to the limbal region, which has the effect of having the force transmitted to the tissue proximate to the limbal tissue, such as the trabecular meshwork, Schlemm's canal, or a combination thereof.

In some embodiments, non-invasive mechanical force is applied to a plurality of limbal regions. For example, the limbal region comprises 360° around the cornea. Thus, in some instances, non-invasive mechanical force is applied to at least 90° of limbal region. In other instances, non-invasive mechanical force is applied to at least 180° of limbal region. Still in other instances, non-invasive mechanical force is applied to 360° of limbal region. When non-invasive mechanical force is applied to a plurality of limbal regions, typically each non-invasive mechanical force application is applied to a limbal region that is substantially adjacent to the previous application area often without any significant overlapping area. However, it should be appreciated that the scope of the present invention is not limited to such application and can include application of mechanical force to some or all overlapping areas as well as application of mechanical force to intermittent areas of the limbal region.

While methods of the invention can use any device that is capable of applying non-invasive mechanical force to limbal regions, in some embodiments methods of the invention uses a non-invasive IOP lowering device as disclosed herein.

Typically, non-invasive mechanical force is applied by non-invasively pressing the limbal region repeatedly, for example, by using the devices disclosed herein such that the oscillating probe presses the limbal region at a frequency and amplitude disclosed herein.

Still other aspects of the invention provide a method for slowing or preventing progression of visual field loss in a subject. Such methods typically comprise non-invasively reducing intraocular pressure of the subject by applying non-invasive mechanical force to a tissue proximate to the limbal tissue for a time sufficient to cause decrease in IOP of the subject.

In some embodiments, non-invasive mechanical force is applied using a non-invasive IOP lowering device as disclosed herein.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1:
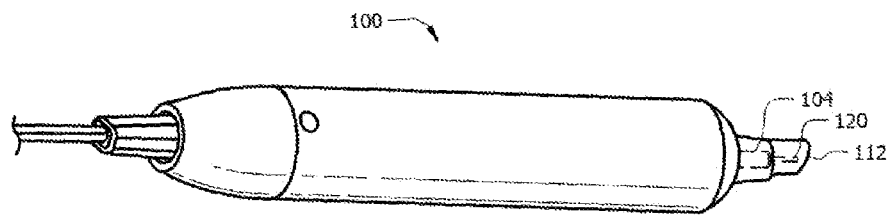
FIG. 1 is an illustration of one particular embodiment of a non-invasive IOP lowering device of the present invention.

Glaucoma is a leading cause of blindness. Topical medications, the primary method of treating high eye pressure in glaucoma, often fail to decrease pressure to a sufficient level. Other treatment methods involve lasers or other invasive or penetrating surgery, which carry with them the potential for serious risk to the eye.

Without being bound by any theory, it is believed that the cause of IOP elevation in glaucoma patients is due to dysfunction of the drainage angle of the eye. Aqueous humor typically flows to the trabecular meshwork (TM) cells and then enters Schlemm's canal eventually moving to the collector channels where fluid is absorbed into the vascular system. It has been shown that outflow dysfunction is, at least in part, due to abnormalities of the TM. The cells that make up the TM are complex and true understanding of the structure and microenvironment physiology of this region is unclear. These cells share characteristics of endothelial cells and their function is regulated by regional proteins, which can lead to both increased or decreased outflow of aqueous humor out of the anterior chamber.

Endothelial cells are known to secrete specific proteins when exposed to shear forces or alternating pressure gradients. TM cells also secrete proteins when exposed to similar stressors. It is believed that these proteins can act to decrease pressure through remodulation of the TM cells and surrounding extracellular matrix. Multiple reports have documented a decrease in IOP in both normal eyes, as well as eyes suffering from glaucoma, after undergoing cataract extraction. The process of removing a cataract from the eye is believed to stress the TM in a way that induces the production of stress proteins that results in a decrease in IOP. Through use of cultured TM cells, a link has been shown between stressing the TM and secretion of interleukin 1 (IL-1), as well as Endothelial leukocyte-adhesion molecule (ELAM)-1.

The present inventor has discovered that similar changes to the TM can be induced to in vivo eyes through external application of an oscillatory force focused over the limbus, which overlies the TM. Without being bound by any theory, it is believed that this type of treatment leads to remodeling of the TM and surrounding ECM thereby leading to increased outflow of aqueous humor and decreased IOP. In some embodiments, the application of force is focused without causing any significant heating of tissue, vibration of surrounding tissues, or injury to surface cells at the site of treatment.

In some aspects of the invention, a non-invasive IOP lowering device is a machine that applies repeated force to tissue at a desired or set frequency and amplitude. Accordingly, other aspects of the invention provide methods for modifying internal ocular tissue through non-invasive treatment. As used herein "non-invasive" refers to a procedure which does not penetrate or break the cell membrane, skin or a body cavity, i.e., it doesn't require an incision (i.e., invasive) into the cell or body, or the removal of biological tissue.

Some aspects of the non-invasive IOP lowering device of the invention will now be described with regard to the accompanying drawings, which assist in illustrating various features of the invention. However, it should be appreciated that the drawings are provided solely for the purpose of merely illustrating some aspects of the present invention and do not constitute limitations on the scope thereof. One particular embodiment of a non-invasive IOP lowering device of the present invention is illustrated in FIGS. 1-3.

Figure 2A:
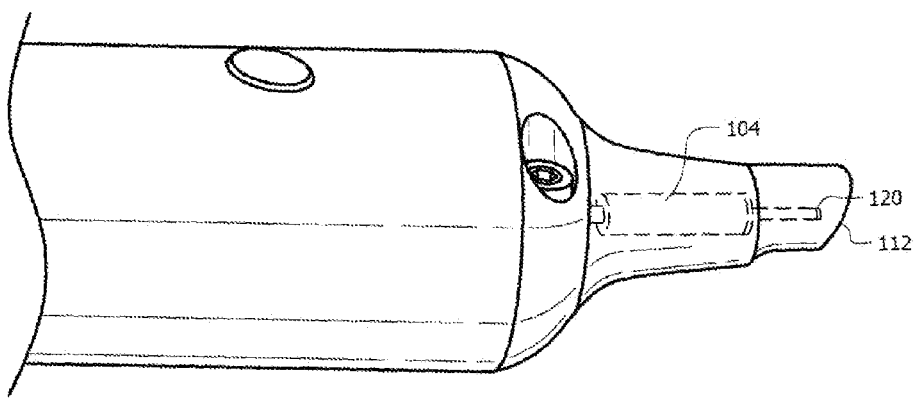
FIGS. 2A, 2B, and 2C are close-up views of an oscillating element of the device shown in FIG. 1.
Figure 2B:
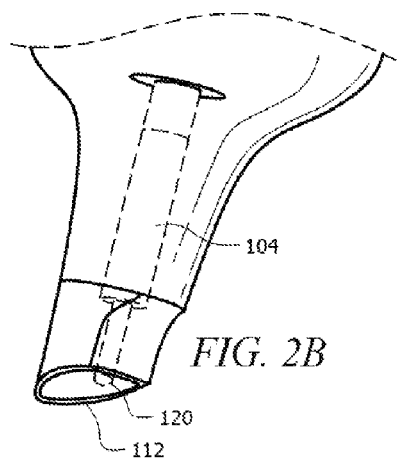
Figure 2C:
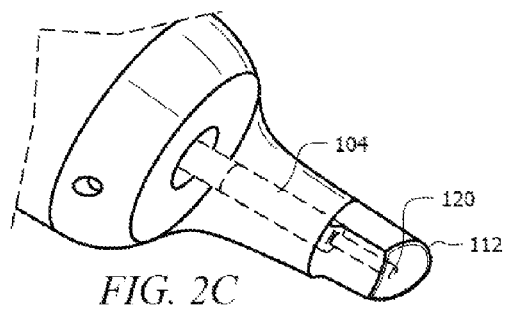
Figure 3:
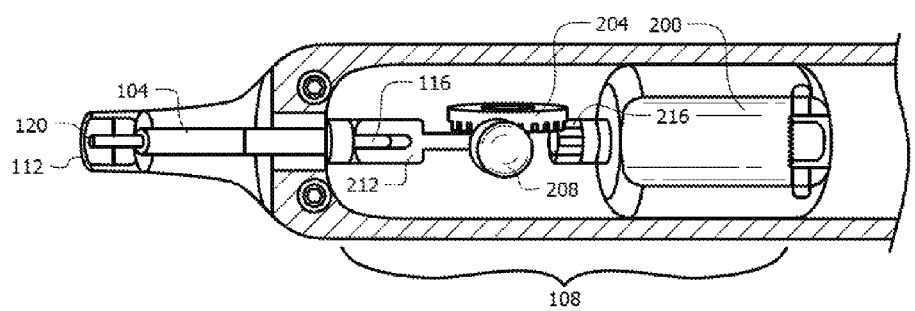
FIG. 3 is a cut away view of the device shown in FIG. 1.

Referring to FIGS. 1-3, in some embodiments a non-invasive IOP lowering device 100 of the invention comprises an oscillating element 104, an oscillating mechanism 108, and a corneal positioning element 112. Oscillating element 104 comprises a proximal end 116 and a terminal (or oscillating) probe 120. Terminal probe 120 is adapted to be in contact with an ocular surface (not shown) and is adapted to non-invasively transmit mechanical force to the tissue proximate to the limbal tissue during operation. Accordingly, terminal probe 120 typically comprises a substantially non-abrasive material so that it does not damage the ocular surface or tissue. Moreover, the tip of terminal probe 120 generally comprises a smooth surface.

As shown in FIG. 3, proximal end 116 is operatively connected to oscillating mechanism 108. In this embodiment, oscillating mechanism 108 comprises a motor 200, a first gear 204, a second gear 208, and a linker 212 that is connected to the proximal end 116. A pair of gears (e.g., first gear 204 and second gear 208) transforms the circular motion of motor 200 to a transversal motion. Motor 200 can be any electric motor that can be operated by alternating or direct current. In FIGS. 1-3, circular motion of motor 200 is transformed to a transverse motion by a pair of gears 204 and 208. As motor 200 spins, it spins cog 216, which in turn spins first gear 204. Cogs of first gear 204 are operatively connected to cogs of second gear 208. Linker 212 is operatively connected in a slightly off-center position of second gear 208. By connecting linker 212 to second gear 208 in this manner, circular motion of second gear 208 generates transverse motion of linker, which in turn provides transverse motion of terminal probe 120. The amount of transverse motion can be controlled by the amount of displacement of linker 212 from second gear's center.

Referring again to FIGS. 1-3, in some embodiments, non-invasive intraocular pressure lowering device 100 further comprises corneal positioning element 112. Corneal positioning element 112 is adapted to prevent oscillating element 104 from penetrating or damaging the ocular surface tissue during operation of device 100. In some embodiments, corneal positioning element 112 is also adapted to guide proper placement of the terminal probe 120 over the target tissue or area. In some embodiments, corneal positioning element 112 is shaped to substantially conform to ocular surface at the limbal region of the eye. The length of corneal positioning element 112 relative to oscillating element 104 is such that terminal probe 120 is prevented from damaging or penetrating ocular surface tissue.

Additional objects, advantages, and novel features of this invention will become apparent to those skilled in the art upon examination of the following examples thereof, which are not intended to be limiting.

EXAMPLES

Example 1

All studies were conducted in accordance with the Association for Research in Vision and Ophthalmology policies for the Care and Use of Laboratory Animals and the protocol was approved by the University of Colorado Institutional Animal Care and Use Committee. Nine Brown Norway rats were housed in an animal lab facility and each received an anterior segment biomicroscopy exam to ensure normal ocular surface status prior to enrollment. All animals had normal pressures at enrollment and were housed in the same facility receiving identical diets throughout the study.

The device used for this clinical study was designed by the present inventor and includes an electronically powered oscillator. The oscillator is attached to a specially designed terminal probe covered by a sleeve or a corneal positioning element. Typically, the tip of the probe is designed to conform to the anatomy of the limbus. The mechanical movement of the device is dependent on a circuit that alternates power to a mechanical coupler, which moves the terminal probe up and down (i.e., axially) in a fashion modifiable by the operator. The sleeve was contacted and positioned such that the oscillating probe tip applied mechanical force to a desired area of the rat eye. Contact was limited to about 0.5 mm (in diameter) area for each application and the depth of oscillatory migration was about 0.5 mm so as to limit motion of the entire eye and focus energy on the targeted tissue. The device was positioned to the study eye (one eye of each rat randomized by coin flip) and non-invasive mechanical force was applied by bringing the oscillating probe tip in to contact with the limbus at a set frequency for 30 seconds at a time. Subsequent applications in the same eye took place adjacent to the previous treatment spot without any significant overlapping. Topical anesthesia (numbing agent) using lidocaine gel was applied to the surface of the eye prior to all treatments. Systemic (whole body) anesthesia for this procedure involved use of Propofol (2-15 mg/kg; intravenous (IV)) after placing each rat in a restrainer with a catheter placed in a tail vein. Gycopyrolate at a dose of 0.01-0.02 mg/kg SQ (under the skin) was used as a supplement when needed.

Nine rats were treated with the device using a frequency ranging between 20 Hz and 1 kHz and covering surface area over the limbus ranging from 90 degrees to 360 degrees.

Intraocular pressure was checked immediately after induction of anesthesia using a tonopen handheld applanator and pneumatonometer, both of which are FDA approved for use in humans and were used daily with topical anesthesia according to the procedure described by Moore et al. in "Noninvasive Measurement of Rat Intraocular Pressure With the Tono-Pen," *Investigative Ophthalmology & Visual Science,* 1993, 34 (2), 363-9. These devices have also been used successfully in Brown Norway rat studies. Each pressure check represents the average of three consecutive measurements. The untreated eye also underwent pressure check as noted for the study eye. A second and third pressure check was performed 2 minutes and 15 minutes after each treatment. A second session of IOP check was performed one week later. Acetominophen 450 mg/100 mL was administered in drinking water dosed continuously for 48 hrs pre and post each procedure.

Results

Each rat tolerated the anesthesia and treatments without complications. No external ocular pathology or cataract formation was noted after the treatments and the rats maintained normal activity and dietary habits in their cages for the duration of follow-up. Dilation at the end of the study revealed normal retinal anatomy with no detachments or hemorrhages. Prior to initial treatment, the average IOP (mm Hg, SD) was (28.22±1.48) and (27.78±1.47) for the study and control eyes, respectively. The average initial IOP check 2 minutes after treatment was (26.67±1.80) for the treatment eyes and (27.67±1.49) for the control eyes. IOP check at 15 minutes revealed average pressures of (25.56±1.59) for the treated eyes and (27.33±1.05) for the control eyes. After one week, the treatment eyes had an average IOP of (21.56±1.13) and the control eyes had an average IOP of (27.89±0.99). Below is the actual IOP data for each subject. IOP measurements show treated eye readings first and then control eye readings.

|  | STUDY | CONTROL |
|---|---|---|
| Rat A | (27, 26, 24, 22) | (28, 28, 27, 29) |
| Rat B | (28, 26, 25, 21) | (29, 30, 29, 29) |
| Rat C | (27, 24, 23, 23) | (27, 27, 28, 27) |
| Rat D | (28, 27, 25, 22) | (29, 29, 27, 28) |
| Rat E | (29, 26, 26, 20) | (30, 28, 28, 27) |
| Rat F | (27, 26, 25, 22) | (26, 27, 27, 28) |
| Rat G | (30, 29, 27, 23) | (29, 29, 28, 29) |
| Rat H | (31, 30, 28, 21) | (26, 26, 27, 28) |
| Rat J | (27, 26, 27, 20) | (26, 25, 25, 26) |

Overall Treatment Eyes:

Base line (BL): 28.22 ± 1.48    after 2 m: 26.67 ± 1.80    after 15 m: 25.56 ± 1.59
after 1 week: 21.56 ± 1.13

Overall Control Eyes:

BL: 27.78 ± 1.47    after 2 m: 27.67 ± 1.49    after 15 m: 27.33 ± 1.05
after 1 week: 27.89 ± 0.99

Treated Eyes:

p = 0.06 BL vs 2 m    p = 0.002 BL vs 15 m    p < 0.001 BL vs 1 wk

Control Eyes:

p = 0.88 BL vs 2 m    p = 0.47 BL vs 15 m    p = 0.85 BL vs 1 wk

Example 2

The effects of mechanical oscillations on the aqueous humor outflow of rabbit eyes were investigated. Each rabbit received an anterior segment biomicroscopy exam (eye exam) to assure normal ocular surface status prior to enrollment. Each group of rabbits was housed in the same facility and received identical diets throughout the study.

The present inventor has discovered that the eye pressure of glaucoma patients decreases significantly after removal of cataracts. This was shown in studies to be due to increased protein production in eye tissue cells. The device used for cataract extraction moves back and forth at a range between 25 and 40 kHz. Without being bound by any theory, this movement is believed to lead to the production of proteins around TM cells, which then opens the drain of the eye. Unfortunately, cataract surgery is an invasive procedure (requires an opening in the eye) and is not appropriate for all those who have glaucoma. The present inventor has discovered that a device that causes mechanical movement of the TM cells through a non-invasive route can be used alternative to cataract surgery.

The device was used to apply an oscillating probe to the area of the limbus (the limbus is the area where the cornea, which is the clear tissue in front of the iris, and the sclera, which is the white part of the eye, meet). The device used for this clinical study, referred to as a mechanical oscillator, is composed of an electricity-powered oscillator. The device includes a mechanical drive (oscillating mechanism), which is attached to a terminal probe covered by a plastic sleeve (corneal positioning element). The mechanical movement of the device is powered by electricity, which then feeds into a circuit that alternates power to a mechanical coupler that moves the terminal probe. The sleeve and oscillating tip are the only components that came into contact with the rabbit eye. Contact was limited to a 0.5-1.0 mm area for each application and the depth of oscillatory migration was 0.3-0.5 mm so as to limit motion of the entire eye and focus energy on the targeted tissue. This study also provided a safety study with repeated slit lamp examination of the eye as well as tissue studies to detail any trauma to the ocular surface. No trauma was observed to local tissue as the eye is very elastic and allows for free indentation. The study involved eight (8) rabbits with one eye randomized to treatment using the device at set frequency.

Method of Treatment

Topical anesthesia using lidocaine gel on the ocular surface was applied prior to all treatments. Systemic anesthesia for this survival procedure involved use of Isoflurane. Each procedure required 2 minutes (including time for sampling of aqueous fluid) from start to completion. Eye pressure was measured using a tonopen, which is an FDA approved device used in human and animal studies to measure eye pressure by externally depressing the tissue of the eye until the digital readout captures internal pressure. A single drop of antibiotic (vigamox) was placed on the cornea along with lidocaine gel prior to treatment. The device was placed over the limbus area of each rabbit followed by application of mechanical oscillation force for 360 degrees using consecutive non-overlapping points of contact. This required about 60-90 seconds of time for each eye treated. For fluid collection, a 30 gauge needle on a TB syringe was used with entry through the limbus (where the cornea and sclera meet) with a total of 50-100 microliters aspirated. This method is routinely used in humans for both diagnostic or study purposes.

The rabbits then underwent recheck of the eye pressures at week one, week four, week eight and week twelve after the initial treatment. Each pressure check was conducted under isoflurane treatment as noted above. Collection of aqueous fluid was performed on each eye and after each treatment as noted above. At the week twelve check, and after a final slit lamp exam, each animal was anesthetized with 25 mg/kg of ketamine hydrochloride and 5 mg/kg of xylazine hydrochloride followed by euthanasia with pentobarbital (150 mg/kg) IV by ear vein. Histology was performed on the enucleated eyes.

Results

Figure 4:
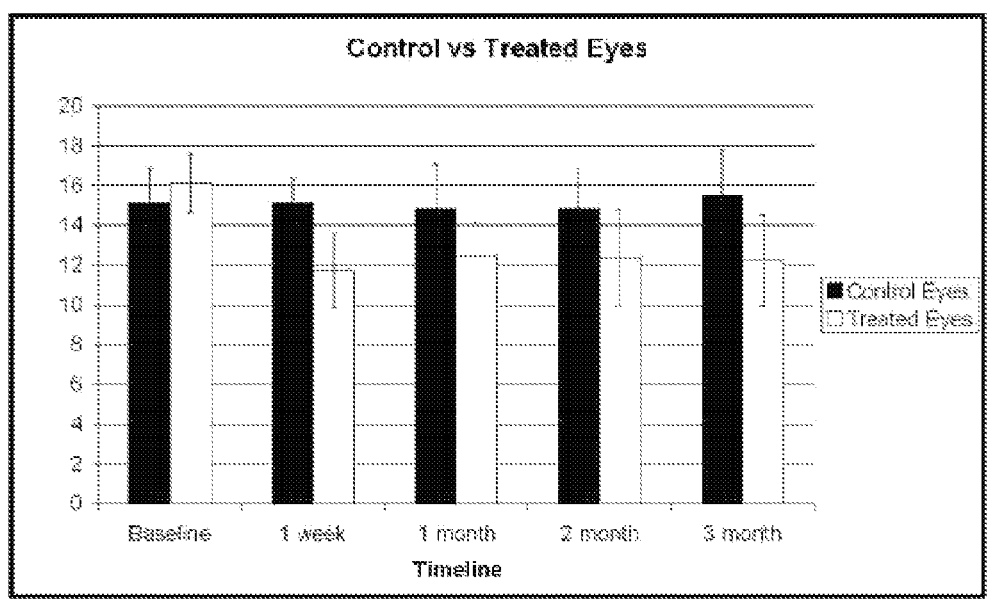
FIG. 4 is a graph of IOP showing the results of a long-term rabbit study using the device of FIG. 1.

As shown in FIG. 4, treated eyes experienced a decrease in intraocular pressure from 16.13±1.46 to 12.25±2.31. This was a 3.88 point (24%) decrease in intraocular pressure. In contrast, control eyes did not experience any significant decrease in intraocular pressure from baseline. In addition, the level of MMP2 in the aqueous humor of treated rabbits increased significantly between pre treatment levels and week one levels. MMP2 staining increased and TIMP2 staining remained stable in the tissues of treated eyes compared to control eyes. These findings were statistically significant.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A non-invasive intraocular pressure lowering device comprising:
    an oscillating element comprising a proximal end, a distal end, and a terminal probe at the distal end, wherein the terminal probe is adapted to be in contact with an ocular surface and is adapted to non-invasively transmit mechanical force to a tissue proximate to a limbal region during operation;
    a motor that is operatively connected to the proximal end of said oscillating element such that when the motor is in operation said oscillating element oscillates at a frequency ranging from 1 Hz to 1 kHz and moves axially and intermittently to apply force to the ocular surface to transmit non-invasive and intermittent mechanical force to the tissue proximate to the limbal region, wherein the motor is configured to transmit mechanical force to the tissue without significant heating of ocular tissue; and
    a positioning element at the distal end of the oscillating element to prevent the terminal probe from penetrating the ocular surface tissue during operation of said device, wherein the positioning element has an ocular contact surface with an opening and the terminal probe extends through the opening in the ocular contact surface during at least a portion of the oscillatory movement of the oscillating element.

2. The non-invasive intraocular pressure lowering device of claim 1, wherein said positioning element is shaped to complement the ocular surface at the limbal region of the eye.

3. The non-invasive intraocular pressure lowering device of claim 1, wherein the oscillation frequency of said oscillating element ranges from 100 Hz to 900 Hz.

4. The non-invasive intraocular pressure lowering device of claim 1, wherein the axial movement of said oscillating element ranges from 0.1 mm to 1 mm.

5. The non-invasive intraocular pressure lowering device of claim 1, wherein the area of the terminal probe that contacts the ocular surface has a mean diameter of from 0.2 mm to 0.5 mm.

6. The non-invasive intraocular pressure lowering device according to claim 1, wherein the positioning element is disposed about a distal portion of the oscillating element and the oscillating element is configured to move reciprocally within the positioning element and the terminal probe extends beyond the ocular contact surface during part of the reciprocating movement of the oscillating element.

7. The non-invasive intraocular pressure lowering device according to claim 1, wherein the positioning element is shaped to complement the shape of the limbus and position the terminal probe on the limbus.

8. The non-invasive intraocular pressure lowering device according to claim 1, further comprising gears wherein the motor produces rotational motion and the oscillating element is connected to the motor by the gears and the gears convert the rotational motion produced by the motor into a reciprocating motion of the oscillating element.

9. The non-invasive intraocular pressure lowering device according to claim 1 wherein the ocular contact surface of the positioning element is at an angle to the perpendicular of the oscillating element, whereby the angle facilitates conformity of the ocular contact surface to the ocular surface of the subject when the intraocular pressure lowering device is placed in contact with the limbal region of the eye of the subject.

10. A method for reducing intraocular pressure of a subject, said method comprising using a device to apply a non-invasive mechanical force oscillating at a frequency of 1 Hz to 1 kHz to a limbal region of an ocular surface of the subject for a predetermined period of time to cause a decrease in the intraocular pressure of said subject, wherein the device comprises:
an oscillating element comprising a proximal end and a terminal probe, wherein the terminal probe is adapted to be in contact with the limbal region of the ocular surface and is adapted to non-invasively transmit mechanical force to a tissue proximate to a limbal region during operation;
a motor that is operatively connected to the proximal end of said oscillating element such that when the motor is in operation said oscillating element oscillates at a frequency ranging from 1 Hz to 1 kHz and moves axially to apply force to the ocular surface to transmit non-invasive and intermittent mechanical force to the tissue proximate to the limbal region; and
a positioning element at the distal end of the oscillating element to prevent the terminal probe from penetrating the ocular surface tissue during operation of said device, wherein the positioning element has an ocular contact surface with an opening and the terminal probe extends through the opening in the ocular contact surface during at least a portion of the oscillatory movement of the oscillating element.

11. The method of claim 10, wherein the non-invasive mechanical force is transmitted to the tissue comprising trabecular meshwork, Schlemm's canal, or a combination thereof.

12. The method of claim 10, wherein the non-invasive mechanical force is applied to a plurality of limbal regions.

13. The method of claim 12, wherein the limbal region is repeatedly pressed non-invasively from 0.1 mm to 1 mm by the oscillation of the terminal probe.

14. The method of claim 12, wherein the limbal region is repeatedly pressed non-invasively at a frequency of from 100 Hz to 900 Hz.

15. A method for slowing or preventing progression of visual field loss in a subject, said method comprising non-invasively reducing intraocular pressure of the subject by applying non-invasive mechanical force oscillating at a frequency of 1 Hz to 1 kHz to a tissue proximate to a limbal region for a predetermined period of time to cause decrease in intraocular pressure of said subject, wherein the mechanical force is applied using an intraocular pressure lowering device having an oscillating element comprising a terminal probe with a diameter from 0.2 mm to 0.5 mm wherein the intraocular pressure lowering device comprises a positioning element at the distal end of the oscillating element to prevent the terminal probe from penetrating the ocular surface tissue during operation of said device, wherein the positioning element has an ocular contact surface with an opening and the terminal probe extends through the opening in the ocular contact surface during at least a portion of the oscillatory movement of the oscillating element.

16. The method of claim 15, wherein said step of applying non-invasive mechanical force comprises contacting an ocular surface in the limbal region using the non-invasive intraocular pressure lowering device comprising:
the oscillating element comprising a proximal end and the terminal probe, wherein the terminal probe is adapted to be in contact with an ocular surface and is adapted to non-invasively transmit mechanical force to the tissue proximate to the limbal tissue during operation;
a motor that is operatively connected to the proximal end of said oscillating element such that when the motor is in operation said oscillating element moves axially and intermittently contacts the ocular surface to transmit non-invasive and intermittent mechanical force to the tissue proximate to the limbal tissue, and
a positioning element that is adapted to prevent said oscillating element from penetrating the ocular surface tissue during operation of said device.

17. A non-invasive intraocular pressure lowering device comprising:
a rod comprising a proximal end and a terminal probe, wherein the terminal probe is adapted to be in contact with an ocular surface and is adapted to non-invasively transmit mechanical force to a tissue proximate to a limbal region during operation;
an motor that is connected to the proximal end of the rod such that when the motor is in operation the rod moves in a reciprocating motion along the axis of the rod at a frequency ranging from 1 Hz to 1 kHz and to apply an intermittent compressive force to the ocular surface to transmit non-invasive and intermittent mechanical force to the tissue proximate to the limbal region; and
a positioning element at the distal end of the rod and disposed around the terminal probe to prevent the terminal probe from penetrating the ocular surface tissue during operation of the device, wherein the positioning element has an ocular contact surface and the terminal probe extends through the ocular contact surface during at least a portion of the oscillatory movement of the rod.

18. The non-invasive intraocular pressure lowering device according to claim 17 wherein the frequency of the device is adjustable.

19. The non-invasive intraocular pressure lowering device according to claim 17 wherein the displacement of the terminal probe is adjustable.

20. The non-invasive intraocular pressure lowering device according to claim 17 wherein the displacement of the terminal probe is between 0.1 mm to 1 mm.

\* \* \* \* \*